United States Patent [19]
Takahashi et al.

[11] Patent Number: 5,561,208
[45] Date of Patent: Oct. 1, 1996

[54] MEDICAL IMPLEMENT, POLYMER COMPOSITION, AND OPTICAL MATERIAL

[75] Inventors: Nobukazu Takahashi; Tohru Hosaka, Yokohama; Koji Minami, all of Yokohama; Yuichiro Konishi; Teiji Kohara, both of Kawasaki; Tadao Natsuume, Yokosuka, all of Japan

[73] Assignee: Nippon Zeon Co., Ltd., Tokyo, Japan

[21] Appl. No.: 510,306

[22] Filed: Aug. 2, 1995

Related U.S. Application Data

[62] Division of Ser. No. 24,294, Mar. 1, 1993, Pat. No. 5,468,803.

[30] Foreign Application Priority Data

| Mar. 3, 1992 | [JP] | Japan | 4-080330 |
| May 21, 1992 | [JP] | Japan | 4-154454 |
| Dec. 28, 1992 | [JP] | Japan | 4-361130 |

[51] Int. Cl.$^6$ .............................. C08F 32/08; C08L 9/06
[52] U.S. Cl. .................... 526/281; 524/81; 524/553; 526/340; 526/347; 526/280
[58] Field of Search ....................... 526/281, 280, 526/340, 347; 524/553, 81

[56] References Cited

U.S. PATENT DOCUMENTS

| 5,003,019 | 3/1991 | Ishimaru | 526/281 |
| 5,204,427 | 4/1993 | Torii | 526/282 |
| 5,218,049 | 6/1993 | Yamamoto | 525/97 |

FOREIGN PATENT DOCUMENTS

| 0226956 | 7/1987 | European Pat. Off. . |
| 0384694 | 8/1990 | European Pat. Off. . |
| 0387662 | 9/1990 | European Pat. Off. . |
| 0386896 | 9/1990 | European Pat. Off. . |
| 0426142 | 5/1991 | European Pat. Off. . |
| 0497567 | 8/1992 | European Pat. Off. . |
| 0498564 | 8/1992 | European Pat. Off. . |
| 0524802 | 1/1993 | European Pat. Off. . |

OTHER PUBLICATIONS

JP-A-3 068 363 (Daikyo Gum Seiko KK) Derwent Publications Ltd., Abstract.
JP-A-3 275 067 (Nippon Zeon KK) Derwent Publications, Ltd., Abstract.

*Primary Examiner*—Fred Zitomer
*Attorney, Agent, or Firm*—Armstrong, Westerman, Hattori, McLeland & Naughton

[57] ABSTRACT

A polymer composition comprising a thermoplastic norbornene polymer which preferably has a number average molecular weight of 10,00–200,000 as determined by gel permeation chromatography in toluene solvent and calculated as styrene and a content of norbornene polymer components having a number average molecular weight of 2,000 or less of 1% by weight or less, and a compounding ingredient, such as a rubber-like polymer, wherein the compounding ingredient is preferably dispersed in the form of microdomains in the norbornene polymer; and medical implements and optical naturals formed essentially of the composition.

21 Claims, No Drawings

5,561,208

MEDICAL IMPLEMENT, POLYMER COMPOSITION, AND OPTICAL MATERIAL

This is a division of application Ser. No. 08/024,294 filed Mar. 1, 1993 U.S. Pat. No. 5,468,803.

BACKGROUND OF THE INVENTION

1. Field of the Invention

The present invention relates to medical implements, and optical materials, formed essentially of a thermoplastic norbornene polymer. In more particular, it relates to medical implements, and compositions with excellent adhesive property, formed essentially of a thermoplastic norbornene polymer which does not cause the deterioration of medical agents that come into contact therewith, and optical materials formed essentially thereof.

2. Related Art

Medical implements are recently shifting toward those of disposable type in order to prevent secondary infections by various viruses caused by their repeated use. With regard to injection drugs, for example, though they were previously used after sucked into a syringe from a sterilized ampoule at the time of injection, recently prefilled syringes, into which an injection drug has been sucked in advance, have come into wide use and the syringes after injection have come to be discarded.

Medical containers for drugs require transparency higher than a certain degree to allow easy visual confirmation of the contents. Previously, glass, polyethylene, polypropylene, and poly(vinyl chloride) have mainly been used therefore. However, glass is fragile, heavy, and alkali ions tend to dissolve out therefrom. Further, it often causes difficulties in throwaway uses because glass is difficult to burn away and its broken pieces are danger to dispose of. Polyethylene and polypropylene are poor in heat resistance, hence cannot be steam-sterilized, and further sometimes low molecular organic components dissolve out therefrom. Poly(vinyl chloride) is poor in heat resistance, and chlorine tends to dissolve out into the content to cause its deterioration.

On the other hand, poly(methyl methacrylate) (PPMA) and polycarbonate (PC) are known to be used as optical materials. However, though PMMA is excellent in transparency it is rather unsatisfactory in heat resistance and moisture resistance, whereas PC is more excellent in heat resistance and moisture resistance than PMMA, but it has a defect of high birefringence. Accordingly, thermoplastic saturated norbornene polymers, which are excellent in all the properties of transparency, heat resistance, moisture resistance and low birefringence, have come to attract attention as optical materials.

However, thermoplastic saturated norbornene polymers have a problem in that, when used as optical materials, they show poor adhesion to adhesives, coating materials used for coloring, ultraviolet curable coating materials used for protective coating or for forming fine structures, various kinds of inorganic or organic film, and like materials. Various treatments with primes and chemicals as well as actinic energy ray treatments have been studied for the purpose of improving adhesiveness. Addition of these treatments to the steps of production or fabrication of molded articles, however, is unfavorable from the viewpoint of production efficiency.

Accordingly, some attempts have been made to improve the adhesiveness of thermoplastic saturated norbornene polymers by modification of the polymer or incorporation of compounding ingredients into the polymer.

For example, it is disclosed to graft-polymerize 1–40% by weight of a rubber-like polymer to a thermoplastic saturated norbornene polymer (Japanese Patent Kokai (Laid-open) No. 3-54220). This method, however, is not satisfactory in point of production efficiency. Moreover, the polymers obtainable are not always transparent.

It is also disclosed that addition of 1–50% by weight of a rubber-like polymer to a thermoplastic saturated norbornene polymer can give a composition with increased adhesiveness to metals and that the composition can be made transparent by using a rubber-like polymer that has a refractive index near to that of the norbornene polymer (Japanese Patent Kokai (Laid-open) No. 3-112646). In this case, however, a large amount of a rubber-like polymer must be added to a thermoplastic norbornene polymer, which causes a problem of lowering of the glass transition temperature (Tg).

SUMMARY OF INVENTION

As the result of extensive study, the present inventors have found that molded articles for medical use formed essentially of a thermoplastic norbornene polymer undergo no deformation even in sterilization, and neither dissolve out impurities nor adsorb drug components. At the same time the inventors have found that a thermoplastic norbornene polymer composition suitable to use for medical implements is excellent in adhesive property and also can be used as an optical material. The present invention has been accomplished on the basis of the above findings.

DETAILED DESCRIPTION OF PREFERRED EMBODIMENTS

Thus, according to the present invention, there are provided medical implements formed essentially of a thermoplastic norbornene polymer, a thermoplastic norbornene polymer composition comprising a thermoplastic saturated norbornene polymer containing a compounding ingredient incompatible therewith, wherein the compounding ingredient is dispersed in the form of microdomains; and optical materials formed essentially of the polymer composition.

Thermoplastic norbornene polymer

The thermoplastic norbornene polymer referred to in the present invention is known to the art from, for example, Japanese Patent Kokai (Laid-open) Nos. 3-14882, 3-122137 and 4-63807. Specific examples thereof include ring-opening polymers of norbornene group monomers, the hydrogenation products thereof, addition polymers of norbornene group monomers, and addition polymers of norbornene group monomers with olefins.

The norbornene group monomer is also known to the art from, for example, the above-mentioned Japanese Patents Kokai and Japanese Patent Kokai (Laid-open) Nos. 2-227424 and 2-276842. Specific examples thereof include norbornene, the alkyl, alkylidene or aromatic group-substituted derivatives thereof, and the derivatives of these substituted or unsubstituted olefins substituted with polar groups such as halogen, hydroxyl, ester, alkoxy, cyano, amido, imido, and silyl, for example, 2-norbornene, 5-methyl-2-norbornene, 5,5-dimethyl-2-norbornene, 5-ethyl-2-norbornene, 5-butyl-2-norbornene, 5-ethylidene-2-norbornene, 5-methoxycarbonyl-2-norbornene, 5-cyano-2-norbornene, 5-methyl-5-methoxycarbonyl- 2-norbornene, 5-phenyl-2-norbornene, 5-phenyl-5-methyl- 2-norbornene, 5-hexyl-2-norbornene, 5-octyl-2-norbornene, and 5-octadecyl-2-norbornene; monomers formed by addition of one or more cyclopentadiene to norbornene, and their derivatives and substitution products similar to those mentioned above, for example, 1,4:5,8-dimethano-1,2,3,4,4a,5,8,8a-octahydro-2,3-cyclopentadienonaphthalene, 6-methyl-1,4:5,8-dimethano-1,4,4a,5,6,7,8,8a-octahydronaphthalene, and 1,4:5,10:6,9-trimethano-1,2,3,4,4a,5,5a,6,9,9a,10,10a-dodecahydro-2,3-cyclopentadienoanthracene; monomers of polycyclic structure which are oligomers of cyclopentadiene, and their derivatives and substitution products similar to those mentioned above, for example, dicyclopentadiene and 2,3-dihydrodicyclopentadiene; and adducts of cyclopentadiene with tetrahydroindene or the like, and their derivatives and substitution products similar to those mentioned above, for example, 1,4-methano-1,4,4a,4b,5,8,8a,9a-octahydrofluorene and 5,8-methano-1,2,3,4,4a,5,8,8a-octahydro-2,3-cyclopentadienonaphthalene.

In the polymerization of the norbornene group monomer in the present invention, other polymerizable cycloolefins or like monomers may be used together to form copolymers within limits not substantially deleterious to the effect of the present invention. As specific examples of copolymerizable cycloolefins in the ring opening polymerization, mention may be made of compounds having at least one reactive double bond, e.g., cyclopentene, cyclooctene, and 5,6-dihydrodicyclopentadiene.

The polymerization of norbornene group monomers may be performed by known methods. In general, a combination of a transition metal compound, such as $TiCl_4$, $WCl_6$, $MoCl_5$, $VCl_5$, $NiCl_2$ and $PdCl_2$, with an alkyl compound of a typical metal, such as Al, Li, Na and Mg, is used as the catalyst for the polymerization. If necessary and desired, the polymer obtained can be hydrogenated, with the aid of a catalyst, such as Ni and Pd, into a thermoplastic norbornene polymer hydrogenation product.

In the previous methods of polymerization known to the art, transition metals originating from the polymerization catalyst remain in the polymer. It is undesirable that the remaining transition metal dissolves out when medical implements contact with a living body, drug, etc., so that it is desirable that substantially no such metals remain in the medical implements. Such substantially metal-free polymers can be obtained, for example, by hydrogenating the polymer using a heterogeneous catalyst comprising a hydrogenation catalyst metal, such as nickel, supported on an adsorbent, such as alumina, having a pore volume of 0.5 $cm^3/g$ or more, preferably 0.7 $cm^3/g$ or more, and a specific surface area of preferably 250 $cm_2/g$ or more, or by treating a solution of the resin with such adsorbents to adsorb metal atoms, or by repeated washing of the resin solution with acidic water and pure water, whereby the content of transition metal atoms originating from polymerization catalyst can be reduced to 1 ppm or less.

The heterogeneous catalyst can be prepared by known methods, for example, according to the methods described in Japanese Patent Kokoku (Post-Exam. Publn.) Nos. 50-15474, 49-32187, 49-11312 and 51-48479, and the adsorbing capacity of the carrier is controlled by regulating the conditions of drying and roasting. In the case of a heterogeneous catalyst comprising nickel supported on activated alumina, for example, aluminum hydroxide powder is suspended to a concentration of 10–20% in an aqueous solution of nickel sulfate or nickel nitrate of a concentration of 10–20% and the suspension is hydrolyzed with sodium hydroxide, whereby nickel hydroxide is supported on the surface of aluminum hydroxide. The resulting powder is collected by filtration and extruded to the form of solid, which is then roasted at 350°–450° C., brought into contact with hydrogen at 100°–200° C. to reduce the surface, and further heated in the presence of oxygen at 80°–120° C. to oxidize the surface of the metal and form oxidized film, whereby an activated alumina-supported nickel catalyst is obtained. Though the surface of nickel is covered by nickel oxide, the nickel oxide is reduced to nickel in the hydrogenation system to function as a catalyst.

Since the fine structure of activated alumina change depending on the extrusion conditions and the temperature and pressure of roasting, the conditions are selected so as to give a pore volume of 0.5 $cm^3/g$ or more, preferably 0.70 $cm^3/g$ or more and a specific surface area of preferably 250 $cm^2/g$ or more. When the hydrogenation is conducted at high temperatures, since the thicker the oxidized film the higher the heat resistance of the film, favorable conditions are to be selected by controlling the oxidation temperature, time, oxygen concentration, and other factors. The intended heterogeneous catalyst may be obtained by pulverizing the roasted product thus obtained.

When a transition metal chloride is used as the transition metal compound of a general polymerization catalyst, usually 2 ppm or more of chlorine atoms remain in the polymer. Since chlorine atoms, similarly to transition metal atoms, desirably do not remain in medical implements, it is desirable to remove them. Chlorine atoms can be removed by the same treatments as those for transition metal atoms, and their residual content can be reduced to 1 ppm or less.

The thermoplastic norbornene polymer used in the present invention should have a glass transition temperature of preferably 105° C. or higher, more preferably 120° C. or higher, particularly preferably 130° C. or higher, for the following reasons. When the polymer is used for medical implements, though sterilization may sometimes be conducted by a method which needs no heating, such as γ-ray irradiation, the most simple and convenient means generally used are those which need heating, particularly boiling and steam sterilization. In sterilization by boiling, no problem arises so long as the thermoplastic norbornene polymer has a glass transition temperature of 105° C. or higher. In steam sterilization, however, the heat resistance necessary for the polymer varies depending on the temperature selected for the sterilization. The steam sterilization most generally used is that at 121° C. which uses an autoclave. To avoid deformation in this steam sterilization, the polymer preferably has a glass transition temperature of 130° C. or higher. In general, the higher the proportion of a monomer having a large number of rings is in the total monomers, the higher the glass transition temperature of the resulting thermoplastic norbornene polymer becomes. For example, the hydrogenation product of the ring-opening polymer of ethyltetracyclododecene, which is a 4-ring compound, has usually a glass transition temperature of 130° C. or higher, while the hydrogenation product of the ring-opening polymer of norbornene, a 2-ring compound, has usually a glass transition temperature of about 30° C. On the other hand, the glass transition temperature of the addition polymer of norbornene is 300° C. or higher, and is sometimes unmeasurable. Too high a glass transition temperature may cause another problem of making injection molding difficult. Accordingly, a thermoplastic norbornene polymer with a glass transition temperature appropriate to intended purposes are to be produced by proper selection of monomers and comonomers.

The thermoplastic norbornene polymer used in the present invention should have a number average molecular weight of 10,000–200,000, preferably 20,000–100,000, more preferably 25,000–50,000, as determined by GPC (gel permeation chromatography) in toluene solvent and calculated as polystyrene. When the number average molecular weight is too low, the polymer is poor in mechanical strength, while when it is too high, the polymer is poor in moldability. The thermoplastic norbornene polymer has a content of polymer components having a molecular weight of 2,000 or less, as determined by high performance liquid chromatography in toluene solvent and calculated as polystyrene, of preferably by weight or less, more preferably 0.5% by weight or less. When the content of the low-molecular weight component is high, the component is liable to dissolve out when the medical implement comes in contact with a living body or a drug.

When the thermoplastic norbornene polymer is hydrogenated, the hydrogenation rate should be at least 90%, preferably at least 95%, more preferably at least 99%, from the viewpoint of resistance to heat degradation and resistance to photo-degradation.

Compounding ingredients

The thermoplastic norbornene polymer, in steam sterilization treatments commonly used for medical implements, shows substantially no shape change, such as deformation, but will sometimes, depending on the treating conditions, develop turbidity to lower its transparency. To avoid this, the polymer is desirably used as a polymer composition by incorporation thereinto a compounding ingredient incompatible with the norbornene polymer. Such compounding ingredients may be either an organic compound or inorganic filler so long as they are capable of being finely dispersed until transparency is developed.

The inorganic filler preferably has an average particle diameter of 1 μm or less, particularly 0.5 μm or less, more particularly 0.2 μm or less. Further, it is desirably transparent and insoluble to water. Examples of the filler include silica, alumina, glass, and the like, each reduced to ultrafine powder of above-mentioned particle diameter.

The organic compound is preferably a high molecular compound that does not substantially deteriorate the medicinal agent which comes in contact with the present medical implement by dissolving out into the agent. To attain a fine dispersion, in particular, a rubber-like polymer with a glass transition temperature of 40° C. or lower is preferred. Some of the rubber-like polymers prepared by block polymerization have two or more glass transition temperatures. In such cases, it suffices that the lower glass transition temperature is 40° C. or lower.

As examples of the high molecular compound used as the compounding ingredient, mention may be made of rubber-like polymers having a glass transition temperature of 20° C. or less, for example, random or block styrene-butadiene copolymer, such as styrene-butadiene rubber and high styrene rubber, and the hydrogenation products of them; isoprene rubber and the hydrogenation products thereof; chloroprene rubber and the hydrogenation products thereof; saturated polyolefin rubber, such as ethylene-propylene copolymer, ethylene-α-olefin copolymer, and propylene-α-olefin copolymer; diene-containing polymers, such as ethylenepropylene-diene copolymer, α-olefin-diene copolymer, diene copolymer, isobutylene-isomer copolymer, and isobutylenediene copolymer, the halogenated products of them, the hydrogenation products of the diene-containing polymers or their halogenated products; acrylonitrile-butadiene copolymers and their hydrogenation products; fluororubbers, such as vinylidene fluoride-ethylene trifluoride copolymer, vinylidene fluoride-propylene hexafluoride copolymer, vinylidene fluoride-propylene hexafluoride-ethylene tetrafluoride copolymer, propylene-ethylene tetrafluoride copolymer; special rubbers, such as urethane rubber, silicone rubber, polyether rubber, chlorosulfonated polyethylene rubber, epichlorohydrin rubber, propylene oxide rubber, and ethylene-acrylic rubber; among norbornene-based rubber-like polymers, e.g., copolymers of a norbornene-group monomer with ethylene or α-olefin. Terpolymers of a norbornene-group monomer, ethylene and α-olefin, ring-opening polymers of a norbornene-group monomer, and the hydrogenation products of ring-opening polymers of a norbornene-group monomer, those which are incompatible with the thermoplastic norbornene polymer that is the main component of the present polymer composition; random copolymers of an aromatic vinyl monomer with a conjugated diene, such as styrene-butadiene-styrene rubber, styrene-isoprene-styrene rubber, and styrene-ethylene-butadienestyrene rubber, and the hydrogenation products of them; thermoplastic elastomers, which include styrene-based thermoplastic elastomers, for example, linear or radial block copolymers of an aromatic vinyl monomer and a conjugated diene, such as styrene-butadiene-styrene rubber, styrene-isoprene-styrene rubber, and styrene-ethylene-butadiene-styrene rubber, and the hydrogenation products of them, and further, urethane-based thermoplastic elastomers, polyamide-based thermoplastic elastomers, polyamide-based thermoplastic elastomers, 1,2-polybutadiene-based thermoplastic elastomers, poly(vinyl chloride)-based thermoplastics elastomers, and fluorine-containing thermoplastic elastomers. As further examples, there may be mentioned such high molecular compounds as polyacrylic or polymethacrylic resins having a cyclic substituent, such as the cyclohexyl group, isobornyl group, tricyclo[4.3.0.1$^{2.5}$]-decane- 3-yl group and tricyclo[4.3.0.1$^{2.5}$]7-decen-3-yl group; copolymers of styrene with an acrylate or methacrylate, such as octyl acrylate, hexyl acrylate, and butyl acrylate;polyamide resins, such as poly(amino-carbonyltetramethylenecarbonylaminomethylene- 1,3-cyclohexylenemethylene); polyester resins such as poly[oxycarbonyl(1,3-phenylene)carbonyloxymethylene(tricyclo[4.3.0.1$^{2.5}$]-3,8-diyl)methylene]; polyether resins such as poly(butylene oxide), poly[oxy(2-methyl- 2-hydroxytrimethylene)oxy(1, 4-phenylene)isopropylidene(1,4-phenylene)]; polycarbonate resins such as poly[oxycarbonyloxy(2-methyl-1,4-cyclohexylene]isopropylidene(3-methyl-1,4-cyclohexylene)]; and polyurethane resins.

Particularly preferred among them are copolymers of an aromatic vinyl monomer with a conjugated diene type monomer, the hydrogenation products thereof, and norbornene-based rubber-like polymers which are incompatible with the thermoplastic norbornene polymer of the present invention, because of their good dispersibility into the thermoplastic norbornene polymers. The copolymers of an aromatic vinyl monomer with a conjugated diene type monomer may be either a block copolymer or a random copolymer. Those polymers whose unsaturated parts other than aromatic rings have ben hydrogenated are more preferred from the viewpoint of weather resistance. Specific examples of such polymers include styrene-butadiene block copolymer, styrene-butadiene-styrene block copolymer, styrene-isoprene block copolymer, styrene-isoprene-styrene block copolymer, the hydrogenation products of them, and styrene-butadiene random copolymer. It is needless to say that, of these polymers, those whose lowest glass transition temperature is 40° C. or less is preferably used.

When the polymer composition of the present invention is formed into the container of drugs, a transparency of a degree is required which permits of confirmation of the quantity and condition of the contents. For this purpose, the difference in refractive index between the compounding ingredient and the thermoplastic norbornene polymer to which the ingredient is added is desirably small. When an ingredient largely different in refractive index is added in a large amount, the resulting composition tends to give opaque articles such that the quantity or condition of the contents cannot be seen from outside; while when such an ingredient is added in too small an amount, the development of turbidity cannot be prevented sufficiently in the steam sterilization treatment.

The thermoplastic norbornene polymer generally lowers its transparency when incorporated with compounding ingredients. The transparency attained varies depending on the kinds of polymers and compounding ingredients and the compounding ratio. When the composition is formed into a sheet of 1 mm thickness, the transparency, in terms of light transmittance in the wave length range of 450–700 nm, is usually 40% or more, preferably 50% or more, more preferably 60% or more.

When the compounding ingredient has been dispersed in the form of microdomains of 0.3 μm or less, particularly 0.2 μm or less in size, the ingredient particles have diameters smaller than the wavelength of visible light and do not scatter light appreciably, so that an excellent transparency is obtained.

The smaller the difference in refractive index between the compounding ingredient and the thermoplastic norbornene polymer is, the more excellent the transparency is. The difference is preferably 0.2 or less, more preferably 0.1 or less, particularly preferably 0.05 or less, still more particularly preferably 0.02 or less, when the compounding amount is 5–0.5% by weight and preferably 0.3 or less, more preferably 0.2 or less, particularly more preferably 0.1 or less, still more particularly 0.05 or less, when the compounding amount is less than 0.5% by weight.

The transparency of the thermoplastic norbornene polymer, in terms of light transmittance in the wave lengthrange of 450–700 nm, is usually 80% or more, when the compounding ingredient is dispersed in the form of microdomains in the polymer and the difference in refractive index between the compounding ingredient and the thermoplastic norbornene polymer is 0.02 or less.

A thermoplastic norbornene polymer has a varied refractive index according to its kind. However, the refractive index of a rubber-like polymer can be changed continuously by, for example, changing the monomer ratio or changing the number of unsaturated bonds in the main chain by hydrogenation or other means. It is desirable to select a rubber-like polymer having an appropriate refractive index in accordance with the refractive index of the thermoplastic norbornene polymer used.

Compounding

In the present invention, 10–0.01% by weight, preferably 5–0.02% by weight, more preferably 1–0.05% by weight, particularly preferably 0.5–0.1% by weight, of a compounding ingredient is added to 90–99.99% by weight, preferably 95–99.98% by weight, more preferably 99–99.95% by weight, particularly preferably 99.5–99.9% by weight, of a thermoplastic norbornene polymer and made to disperse in the norbornene polymer. When the added amount is too large, the resulting composition tends to have low transparency, glass transition temperature and heat resistance. When the amount is too small, substantially no effect of incorporation of the ingredient is obtained.

The method for adding the compounding ingredient is not particularly limited so long as it ensures a sufficient dispersion of the ingredient in the thermoplastic norbornene polymer. When a rubber-like polymer is used as the compounding ingredient, for example, the compounding can be performed by kneading the mixture in a molten state with a mixer or twin-screw kneader or by dispersing its solution in a suitable solvent and then removing the solvent by coagulation, casting or direct drying.

When kneading is adopted, a sufficient shear must be applied at a polymer temperature of Tg+50° C. to Tg+150° C. When the polymer temperature is too low the viscosity becomes too high, making the kneading difficult. When the temperature is too high, the norbornene polymer and the rubber-like polymer tend to deteriorate and the two polymers cannot be blended well owing to the differences in viscosity and melting point.

When the kind and amount of the compounding ingredient are properly controlled, the resulting polymer composition will have a transparency of a degree that permits of confirmation of the quantity and condition of the contents when molded into drug containers. To attain an improved transparency, it is desirable that the compounding ingredient is dispersed in the form of microdomains in the thermoplastic norbornene polymer. When the ingredient is an organic compound, it sometimes does not form microdomains when the compounded amount is large. In the case of a rubber-like polymer, it can be made to form microdomains when added in an amount of 0.8–0.001% by weight. When the compounding amount is small or when no compounding ingredient is added, the polymer may become cloudy and lose transparency through steam sterilization in an autoclave or the like.

For example, in the case of using a Labo-plastomill (mfd. by Toyo Seiki K.K.) for kneading, when kneading is conducted by using the apparatus at the "twin-screw different direction mixer" mode and a number of rotation of 20–30 rpm and adjusting the residence time to about 1–10 min. by controlling the feed rate, usually a rubber-like polymer can be dispersed to form microdomains of 0.3 μm or less in diameter in the thermoplastic norbornene polymer. In a twin-screw kneader, generally, L/D of at least 25, preferably at least 30, is selected and the residence time is adjusted to about 1–10 min. The longer the residence time is, the easier the microdomains can be formed, but the more the norbornene polymer and the rubber-like polymer are liable to deteriorate. Therefore, in dependent of the combination of the norbornene polymer used, rubber-like polymer and the apparatus used for kneading, the number of rotation, residence time and other conditions which accord to the combination should be determined by preliminary kneading.

When a rubber-like polymer is used as the compounding ingredient, the microdomains assume approximately the form of sphere, and the variation of microdomain particle diameters among particles is small. The diameter is usually 0.3 μm or less, preferably 0.2 μm or less. When the particle diameters are in the above-mentioned range, the lowering of transparency of the thermoplastic norbornene polymer composition caused by the addition of rubber-like polymer is small and raises no problem, as described later. In the case of other compounding ingredients, too, it is desirable that the microdomains assume approximately the form of sphere and that the microdomain particles are uniform in particle diameter and have a particle diameter of 0.3 μm or less, particularly 0.2 μm or less. Even when the microdomains are in a form other than a sphere, the ingredient can be suitably used so long as the longest diameter of the microdomain is 0.3 μm or less, particularly 0.2 μm or less.

Additives

The thermoplastic norbornene polymer used in the present invention may be, if necessary and desired, incorporated with various additives. Additives used in the polymer are those which are compatible with the polymer and include, for example, phenol-type or phosphor-containing antioxidants, antistatic agents, ultraviolet absorbers, and lubricants. When sheets are formed by solution casting, a leveling agent is also preferably added to reduce surface roughness. The leveling agent used may be, for example, a leveling agent for paint, such as a fluorine-containing nonionic surface active agent, special acrylic resin-based leveling agent and silicone-based leveling agent. Preferred among item are those which have good compatibility with solvents. However, these additives are liable to dissolve out from the polymer, so that the additives are preferably those having a high molecular weight and preferably added in a relatively small amount.

For example, antioxidants have a relatively low molecular weight and are liable to dissolve out. The dissolution, however, can be prevented if an antioxidant having a molecular weight of 600 or more, preferably 700 or more, is used, and virtually no antioxidant will dissolve out so long as it is added in an amount of 3,000 ppm or less, preferably 1,000 ppm or less, more preferably 500 ppm or less.

Examples of antioxidants having a molecular weight of 600 or more include pentaerythrityl-tetrakis[3-(3,5-di-t-butyl- 4-hydroxyphenyl)propionate], 1,3,5-trimethyl-2,4,6-tris(3,5-di-t-butyl-4-hydroxybenzyl)benzene, tris(3,5-di-t-butyl-4-hydroxybenzyl)isocyanurate, 3,9-bis[1,1-dimethyl-2-[β-(3-t-butyl-4-hydroxy-5-methylphenyl)propionyloxy]ethyl]-2,4,8,10-tetraoxaspiro-[5,5]undecane, 1,6-hexanediol-bis[3-(3,5-di-t-butyl-4-hydroxyphenyl)propionate], 2,2-thiodiethylenebis[3-(3,5-di-t-butyl- 4-hydroxyphenyl)propionate], N,N'-hexamethylenebis(3,5-di-t-butyl-4-hydroxy-hydrocinnamide), and 1-[2-[3-(3,5-di-t-butyl-4-hydroxyphenyl)propionyloxy]ethyl]-4-[3-(3,5-di-t-butyl-4-hydroxyphenyl)propionyloxy]-2,2,6,6-tetramethylpiperidine.

Further, in order to prevent the development of turbidity in steam sterilization, a partial etherification product and/or partial esterification product of a polyhyhdric alcohol may be added to the thermoplastic norbornene polymer in an amount of 5–0.01% by weight, preferably 2–0.05% by weight, more preferably 1.0–0.1% by weight. By the addition, the development of turbidity in steam sterilization can be prevented like by the addition of a compounding ingredient.

As examples of the partial esterification product formed by esterifying part of the alcoholic hydroxyl groups of a polyhydric alcohol, there may be mentioned those known from Japanese Patent Kokai (Laid-open) No. 63-275654, which include glycerol monostearate, glycerol monolaurate, glycerol monobehenate, diglycerol monostearate, glycerol distearate, glycerol dilaurate, pentaerythritol monostearate, pentaerythritol monolaurate, pentaerythritol monobehenate, pentaerythritol distearate, pentaerythritol dilaurate, pentaerythritol tristearate, and dipentaerythritol distearate.

As examples of the partial etherification product formed by etherifying part of the alcoholic hydroxyl groups of a polyhyhdric alcohol, mention may be made of 3-(octyloxy)-1,2-propanediol, 3-(decyloxy)-1,2-propanediol, 3-(lauryloxy)-1,2-propanediol, 3-(4-nonylphenyloxy)-1,2-propanediol, 1,6-dihydroxy-2,2-di(hydroxymethyl)-7-(4-nonylphenyloxy)- 4-oxoheptane, an ether compound obtained by the reaction of the condensation product of p-nonylphenol and formaldehyde with glycidol, an ether compound obtained by the reaction of the condensation product of p-octylphenol and formaldehyde with glycidol, and an ether compound obtained by the reaction of the condensation product of p-octylphenol and dicyclopentadiene with glycidol. Particularly preferred among them are those which have a molecular weight of 500–2,000, particularly 800–1,500. When an additive of a low molecular weight is used in a large amount the additive is liable to dissolve out, so that it is preferable to add an additive of a high molecular weight in a small amount. When the added amount is too small, the effect of preventing the development of turbidity due to steam sterilization obtainable is small.

Molding

The thermoplastic norbornene polymer of the present invention is not particularly limited as to the molding method. Various methods, including injection molding, blow molding, injection blow molding, rotational molding, vacuum forming, extrusion, calendering and solution casting, can be used according to the intended purposes.

The molded articles of the thermoplastic norbornene polymer incorporated with the compounding ingredient of the present invention have substantially the same heat resistance, chemical resistance, dielectric characteristics, and rigidity as those of molded articles of the thermoplastic norbornene polymer containing no such ingredients.

The thermoplastic norbornene polymer of the present invention adsorbs little of chemicals. In particular, the polymer adsorbs little of functional group-containing compounds, such as alcohols, amines, esters, amides, ethers, carboxylic acids and amino acids. Further, the thermoplastic norbornene polymer of the present invention will not bleed organic substances therefrom. Therefore, medicines which come into contact with the polymer undergo no deterioration.

Medical implements

The medical implements of the present invention include, for example, containers of liquid, powder or solid medicines, such as containers of liquid medicines for injection, ampoules, prefilled syringes, bags for infusion solutions, solid medicine containers, ophthalmic preparation containers, and drip transfusion solution containers; food containers; sample containers, such as sampling test tubes for blood examination, blood collecting tubes, and specimen containers; containers for sterilization of medical implements which contact with living bodies, such as scalpels and forceps, and medical materials, such as gauze and contact lenses; medical implements such as syringes; laboratory implements, such as beakers, Petri dishes, and flasks; optical parts, such as plastic lenses for medical tests; piping materials, such as tubes for medical infusion solutions, piping, joints and valves; and artificial organs and their parts, such as denture bases, artificial hearts and artificial roots of teeth. In particular, containers in which medicines, particularly liquid medicines, are stored over a long period, for example, medicine bottles, prefilled syringes, sealed medicine bags, ophthalmic preparation containers, ampoules, vials and infusion solution containers, made of the polymer of the present invention have, besides good transparency and physical properties, favorable properties of dissolving out substantially no impurity from the polymer, adsorbing substantially no medicine, and hence causing little deterioration of medicines, as compared with containers made of prior art polymers.

Primer

In the present invention, it is desirable to form a hard coating layer on the surface parts of the implement of the present invention which do not come into contact with a medicine or living body or with a medical implement that comes into contact with a living body. As described above, when a thermoplastic norbornene polymer is incorporated with a rubber-like polymer, it acquires a good adhesive property. In the case of a thermoplastic norbornene polymer which has not been improved in adhesive property by such means, however, preferably a primer layer is formed in advance on the part to be hard-coated.

The primer used in the present invention consists essentially of a halogenated hydrocarbon polymer which has a molecular weight of usually 5,000–200,000, preferably 10,000–150,000, more preferably 20,000–100,000. Such halogenated hydrocarbon polymers may be, for example, the halogenation products of hydrocarbon polymers obtained by polymerization or copolymerization of hydrocarbon monomers, such as ethylene, propylene, butadiene, isoprene and styrene, or polymers or copolymers of halogen-containing monomers such as vinyl chloride, vinylidene chloride, and chloroprene. Preferred among them are the chlorinated products of hydrocarbon polymers, particularly preferred is chlorinated polypropylene.

The halogen content is 15–55% by weight, preferably 20–45% by weight, more preferably 25–35% by weight. When the molecular weight is too low, the strength of the primer layer tends to be low, while when it is too high, the viscosity of the primer solution tends to be excessively high, resulting in poor operability in coating. When the halogen content is either too high or too low, the adhesion between the primer layer and the surface to be hard-coated and that between the primer layer and hard coating layer tend to be poor.

When an ultraviolet curing hard coating layer is to be formed, a photopolymerizable monomer or a photopolymerizable oligomer described later, particularly monofunctional acrylate monomer, is preferably added in an amount of 2–20% by weight because the adhesion between the primer layer and the hard coating layer is improved thereby.

In the present invention, the primer is used as a primer solution in a solvent. The solvent is not particularly limited so long as it is a substantially poor solvent to thermoplastic saturated norbornene polymer. For example, toluene is a good solvent to thermoplastic saturated norbornene polymer but, when it is diluted to 70% by weight or less with methyl isobuytyl ketone the mixture will not appreciably erode thermoplastic saturated norbornene polymer when applied onto the polymer, so that such mixtures can be used as the solvent for primers. In forming an ultraviolet curing hard coating layer, monofunctional acrylates such as n-butyl methacrylate and isoamyl methacrylate are advantageous as the solvent because they are poor solvents to thermoplastic saturated norbornene polymer and are at the same time reactive diluents which can act as a photopolymerizable monomer when added to the above-mentioned primer.

The concentration of the primer solution is 1–30% by weight, preferably 2–20% by weight, more preferably 3–10% by weight.

Method for forming primer layer

The primer layer formed in the present invention may be obtained by coating a primer solution on a hard coating layer-forming surface formed essentially of thermoplastic saturated norbornene polymer and then thoroughly removing the volatile component of the solvent. When, for example, the above-mentioned reactive diluent alone is used as the solvent for primer, the removing operation is unnecessary.

The method for coating the primer solution is not particularly limited and such methods as, for example, spraying, dipping, spin coating, and roller coating can be used. The method for removing the volatile component of the primer solution is also not particularly limited. The evaporation temperature and time which are necessary for substantially removing the solvent may somewhat vary depending on the kind of the solvent used, the coating amount, and the shape of adhesive surface or hard coating layer-forming surface, but the evaporation conditions are determined such that the temperature is about 120° C. or lower to avoid the thermal deformation of the molded article having the hard coating layer-forming surface and that the solvent can be thoroughly removed. More specifically, the coated primer layer is suitably allowed to stand at 60°–120° C. for about 3–60 min. It is preferably that after removing the volatile component at high temperature, the primer layer is cooled for about 10 sec.–10 min. at room temperature and thus brought down approximately to room temperature.

Though the coating amount is not particularly limited, it is preferably selected so as to give a layer thickness of about 21–10 μm, particularly about 2–5 μm. The removal of volatile components after coating is necessary, it is preferably selected so as to give the above-mentioned thickness after thorough removal of volatiles. When the coating amount of the primer is too small the effect of primer obtained is small, while when the amount is too large the coating is difficult to dry or does not give satisfactory adhesion.

Coating agent

The coating agent used for forming the hard coating layer may be either a silicone-type coating agent or an organic-type coating agent. Silicone-type coating agents are partially hydrolyzed products of silane compounds. Organic-type coating agents include coating agents comprising coating materials based on melamine, alkyd, urethane or acrylic which are cured by heating and ultraviolet curable coating agents comprising multi-functional acrylic monomers or the like which are used by ultraviolet light. Ultraviolet curable coating agents are preferable because they can be cured under conditions that hardly cause the thermal deformation of thermoplastic saturated norbornene polymer and that give sufficient hardness and weather resistance.

The ultraviolet curable coating agent used in the present invention comprises a reactive monomer and/or a reactive oligomer, a photopolymerization initiator, and other additives, together with no solvent or a solvent for dilution.

The reactive monomer is mainly an acrylate. Specific examples include monofunctional acrylate monomers, such as 2-hydroxyethyl methacrylate, 2-hydroxypropyl methacrylate, 2-ethylhexyl methacrylate, phenoxyethyl acrylate, phenoxypropyl acrylate and other higher alkyl acrylates; monofunctional monomers such as styrene and vinylpyrrolidone; and polyfunctional acrylate monomers formed by combining two or more acrylates to polyols, such as ethylene glycol, diethylene glycol, tripropylene glycol, butylene glycol, hexanediol, trimethylolpropane, tetramethylolpropane, and pentaerythritol.

As the reactive oligomers, there may be mentioned polyester acrylates having an acroyl group at the terminal, epoxyacrylates or polyurethane acrylates having an epoxy group in the molecular chain and at the same time an acroyl group at the terminal, unsaturated polyesters having a double bond in the molecular chain, 1,2-polybutadiene, and other oligomers having an epoxy group or a vinylether group.

Examples of the photopolymerization initiator include acetophenones such as 2,2-dimethoxy-2-phenylacetophenone, 2,2-diethoxyacetophenone, and chlorinated acetophenone; benzophenone; benzoins such as benzyl, methyl o-benzoylbenzoate and benzoin alkyl ether; azo compounds such as $\alpha,\alpha'$-azobisisobutyronitrile, 2,2'-azobispropane, and hydrazone; organic peroxides, such as benzoyl peroxide, and di-t-butyl peroxide; and diphenyl disulfides, such as diphenyl disulfides, dibenzyl disulfide, and dibenzoyl disulfide. Further, commercially available products as Darocur-1173 (mfd. by Merck Japan Limited), Darocur-1116 (mfd. by Merck Japan Limited), Irgacure-184 (Ciba Geigy Limited) and Irgacure-651 (Ciba Geigy Limited).

In the present invention, ultraviolet curable coating agents are preferred which comprise a monofunctional acrylate monomer, di- or trifunctional acrylate monomer, tetra or more-functional acrylate monomer, and a photopolymerization initiator.

In the present invention, a photopolymerizable monomer which has one acrylate group is referred to as a monofunctional acrylate monomer, and one which has two acrylate groups as a difunctional acrylate monomer. Analogous naming applies to monomers having a larger number of acrylate groups.

The monofunctional acrylate monomers may be, for example, n-butyl acrylate, isoamyl acrylate, 2-hydroxyethyl methacrylate, 2-hydroxypropyl methacrylate, 2-ethylhexyl methacrylate, phenoxyethyl acrylate, phenoxypropyl acrylate and other higher alkyl acrylates. Acrylates which have a side chain of about 4–6 carbon atoms are preferable to reduce the cure shrinkage of the ultraviolet curing coating agent.

The di- or trifunctional acrylate monomers may be, for example, those formed by combining two or three acrylates to polyols, such as ethylene glycol, diethylene glycol, tripropylene glycol, butylene glycol, neopentyl glycol, hexanediol, trimethylolpropane, tetramethylolpropane, pentaerythritol, and dipentaerythritol.

The tetra or more-functional acrylate monomers may be, for example, those formed by combining 4 or more acrylates to polyols, such as tetramethylolpropane, pentaerythritol and dipentaerythritol.

The mixing ratio of these components in the coating agent, relative to the total weight of the acrylate monomers and the photopolymerization initiator, is normally as follows: 0–80% by weight, preferably 0–60% by weight, of the monofunctional acrylate monomer; 5–70% by weight, preferably 10–50% by weight, of the di- or trifunctional acrylate monomer; 10–80% by weight, preferably 20–75% by weight, of the tetra or more-functional acrylate monomer; and 0.5–10% by weight, preferably 1–5% by weight, of the photopolymerization initiator. When the amount of the tetra or more-functional acrylate monomer is too large, the cure shrinkage increases, while when it is too small, the hardness of the hard coating layer and the curing velocity decrease. When the amount of the monofunctional acrylate monomer is small, the viscosity tends to be high, leading to a poor coating operability. When the amount of the mono-functional acrylate monomer is large, though it decreases the cure shrinkage, it results in the decrease of the amount of the di- or trifunctional acrylate monomer, which lowers the flexibility of the hard coating layer and can cause the development of cracks. Further, in order to attain an improved adhesive property the di- or trifunctional acrylate monomer is used preferably in a large amount.

Further, suitable additives may be added to the hard coating layer so long as they do not adversely affect the adhesiveness and hardness of the layer. For example, the antistatic property of the surface can be improved by addition of suitable surface active agents, e.g., nonionic surface active agents having a good compatibility with ultraviolet curable agents, particularly amine-type surface active agents, and other antistatic agents. Further, wetting between the surface and a substrate and the smoothness of the surface after curing can be improved by addition of fluorine-containing nonionic surface, active agents. In particular, by improvement in the surface smoothness after curing, the slip of the hard coating layer of the surface is improved, and resultantly the molded articles become less susceptible to scratches. Further, appropriate thermoplastic polymers may be added to control the viscosity or improve the adhesiveness. As examples of thermoplastic polymers capable of improving adhesiveness, there may be mentioned, in the case of thermoplastic saturated norbornene polymers, thermoplastic norbornene polymers or polymers similar thereto in structure, e.g., ring-opening polymers of norbornene-group monomers, petroleum resins of dicyclopentadiene type, diene type, aliphatic type and water white type, and the hydrogenation products thereof.

The mixtures of the components described above may be used as such as the ultraviolet curable coating agent. If necessary and desired for better operability or other factors, however, they may be made up into the ultraviolet curable coating agent by dissolving them in a concentration of 1–50% by weight, preferably 5–30% by weight, into a solvent, e.g., alcohols such as methanol, ethanol and propanol; glycols such as ethylene glycol, butanediol and hexanediol; aromatic hydrocarbons such as toluene and xylene; alicyclic hydrocarbons such as cyclohexane and methylcyclohexane; ketones such as methyl isobutyl ketone, methyl ethyl ketone, and acetone; ethers such as n-butyl ether and diethyl ether; esters such as ethyl acetate and butyl acetate; cellosolves such as methylcellosolve and ethylcellosolve; and chlorine-containing solvents such as chloroform and methylene chloride.

Method for forming hard coating layer

In the present invention, the hard coating layer may be formed by applying the ultraviolet curable coating agent onto the hard coating layer forming surface or onto the hard coating layer-forming surface which has been treated with a primer as described above, and then irradiating ultraviolet light to cure the coating agent. When the ultraviolet curable coating agent is used as a solution in a solvent, the volatile components are to be thoroughly removed after the application of the ultraviolet curable coating agent and prior to the subsequent step. When the ultraviolet curable coating agent is cured while containing a large amount of the solvent, the resulting coating film tends to develop cracks and further may fail to attain a high hardness.

The method for applying the ultraviolet curable coating agent is not particularly limited, and such methods as, for example, spraying, dipping, spin coating, and roller coating can be used. The method for removing volatile components is also not particularly limited. The temperature and time which are necessary for substantially removing the solvent by evaporation may somewhat vary depending on the kind of the solvent used, the coating agent, and the shape of hard coating layer-forming surface, but the evaporation conditions are determined such that the temperature is about 120° C. or lower to avoid the thermal deformation of thermoplastic saturated norbornene polymer and that the solvent can be thoroughly removed. More specifically, the solvent is suitably removed at 60°–120° C. for about 3–60 min. It is preferable that after removing the volatile component at high temperature, the coating agent layer is cooled at room temperature for about 10 sec.–10 min. and thus brought down approximately to room temperature.

The coating amount is preferably so selected as to give a coating layer thickness of about 2–300 μm. When the solvent is removed, the coating amount is preferably selected so as to give the above-mentioned thickness after the removal. When the amount of the ultraviolet curable coating agent applied is small, a hard coating layer with a high strength is not obtained, and a sufficient effect of improving the surface hardness is not attained. When the amount is large, on the other hand, the solvent removal and the curing reaction take much time, resulting in poor productivity; sometimes the hard coating layer cures insufficiently and has a low hardness, or it is lacking in flexibility and may develop cracks.

Thereafter, ultraviolet light is irradiated from a light source capable of generating ultraviolet light efficiently, e.g. a high pressure mercury lamp, whereby curing proceeds in a short time to form a hard coating layer having a high hardness. The irradiation intensity of ultraviolet light is selected, when a high pressure mercury lamp is used, from the range of 1,500–20,000 $mJ/cm^2$, preferably 3,000–15,000 $mJ/cm^2$.

The hard coating layer thus cured shows a pencil hardness of 2H or higher, preferably 3H or higher, and an adhesiveness, as determined by the cross-cut peeling test, of 80 squares/100 squares or more, preferably 90 squares/100 squares or more. The layers does not yet scratched in a steel wool test using #0000 steel wool, and does not peel off through steam sterilization. Further, it is neither dissolved nor peeled off by common solvents, machine oil, and the like.

Thus, by providing a hard coating layer to the medical implements of the present invention, their outside surfaces can be made more hard, less susceptible to scratches and more resistant to chemicals. Accordingly, in actual process steps of filling medicines by using a machine, the development of cracks due to the contact of the outside surface with metals or such and the sticking of difficultly removable soils due to machine oils can be suppressed.

Polymer Composition

Among the polymer compositions used for the medical implements of the present invention, those which comprise a thermoplastic norbornene polymer and a compounding ingredient incompatible therewith, wherein the compounding agent is dispersed in the form of microdomains has an excellent transparency and can be used also as an optical material excellent in adhesive property. Particularly preferred as such compositions are those which use a rubber-like polymer as the compounding ingredient, and which comprise the rubber-like polymer in a proportion of preferably 0.001–0.8 part by weight, more preferably 0.003–0.6 part by weight, particularly preferably 0.005–0.4 part by weight, relative to 100 parts by weight of the thermoplastic norbornene polymer.

Polymer compositions used also as optical materials are preferably those in which the difference in refractive index between the thermoplastic norbornene polymer and the compounding ingredient used is 0.02 or less, particularly 0.015 or less, more particularly 0.01 or less, because they have excellent transparency. Though thermoplastic norbornene polymers are varied in refractive index according to their structure, it is practically difficult to select a polymer having a specific refractive index. With regard to a rubber-like polymer, on the other hand, its refractive index can be changed nearly continuously by changing the monomer ratio or changing the number of unsaturated bonds in the main chain by hydrogenation or other means, so that a polymer with a specific refractive index can be selected. It is desirable to select a rubber-like polymer having an appropriate refractive index in accordance with the refractive index of the thermoplastic norbornene polymer used.

In such thermoplastic saturated norbornene polymer compositions, the compounding ingredient is usually dispersed in the form of microdomains having diameters of 0.3 µm or less, preferably 0.2 µm or less, in the matrix of the thermoplastic norbornene polymer. The wave length of the monochromatic light used in information processing devices, such as information disks and infrared sensors, is about 300 nm–1,000 nm and that of visible light is about 400–800 nm. When the compounding ingredient has a particle diameter smaller than the wave length of these light and forms microdomains of 0.3 µm or less, particularly 0.2 µm or less, it hardly scatters these lights. Therefore, the thermoplastic saturated norbornene composition according to the present invention is excellent in transparency.

Though the transparency of the polymer composition of the present invention varies depending on the refractive index and the added amount of the rubber-like polymer, and the diameter and the state of dispersion of the microdomains, the transmittance of light of 400–700 nm of a sheet-formed molded article 3 mm in thickness is usually 50% or more. It can be brought to 80% or more, and further to 90% or more, by regulating the refractive index, added amount and state of dispersion.

The molded articles of the polymer composition of the present invention are excellent in adhesiveness to various materials in various applications as compared with those from thermoplastic saturated norbornene polymers incorporated with no rubber-like polymer: namely, in adhesion, to thermosetting adhesives such as phenolic adhesives, polyester-type adhesives, epoxy adhesives and silicone adhesives, thermoplastic adhesives such as 1 poly(vinyl acetate)-based adhesives, poly(vinyl alcohol)-based adhesives, poly(vinyl chloride)-based adhesives, and nitrocellulose-based adhesives, butadiene-acrylonitrile rubber-based adhesives and neoprene-based adhesives; in coating, to oil paints such as enamel, alcoholic coating materials such as quick-drying varnish and alcohol-soluble phenolic resin varnish, cellulosic coating materials such as ethylcellulose lacquer, synthetic resin coating materials such as vinyl resin varnish, water paints such as synthetic rubber latex paints, and rubber-based paints such as chlorinated rubber paint; in forming hard coating layers and protective coating layers, to thermosetting organic coating agents based on melamine, alkyd, urethane and acryl, polyfunctional acrylic ultraviolet curable organic coating agents and silicone coating agents; in the so-called 2P process wherein fine structures of stampers and the like are transferred to coated materials, to ultraviolet curable acrylic coating materials and reaction curable epoxy coating materials; and when formed into optical disks and the like, to metallic reflecting film formed of metals having high reflectance, such as nickel, aluminum and gold, deposited by vacuum vapor deposition, sputtering, etc., and to magneto-optical recording film formed of Tb—Fe—Co alloy, etc.

The polymer composition of the present invention can be widely used, by virtue of its excellent properties described above, for various articles, which include, in the electric and electronic field, water tanks of steam iron, parts and containers for microwave ovens, printed wiring board, high frequency circuit board, electroconductive, transparent or opaque sheets, diaphragms of speakers, carriers for semiconductor production, covers and decorations of lighting equipment, coating materials for wire, insulating film, condenser film, and sealing agents for electronic elements; industrial parts, such as camera parts, and housings and containers for various measuring instruments and equipment; general goods for daily use, such as various sheets, helmets, protectors and nose-guards of spectacles; and alternate materials for windshield glass and window glass. Further, the composition can be favorably used, by virtue of its excellent transparency, as optical materials, e.g., for substrate of information disks, such as magneto-optical disks, pigment-type disks, compact disks for music, and simultaneous image-sound recording-play-back disks; lenses and mirror lenses for image pickup system or projection system used in cameras, VTR, copying machines, OHP, projection TV and printers; lenses for pick-up of information from information disks and bar codes; lenses of automobile lamps, spectacles and goggles; information transfer parts such as optical fiber and its connectors; and films and sheets in the field of information recording and information display, for example, substrates for information recording of other forms than disks, such as optical cards, liquid crystal substrates, phase films, polarizing films, optical guide sheets, and protective, moisture preventive films.

The present invention will be described in more detail below with reference to Referential Examples, Examples and Comparative Examples. In the Examples, the pencil hardness determination, cross-cut peeling test, steel wool test, and steam treatment were conducted in the following manners.

Pencil hardness determination

The pencil hardness was determined according to JIS K-5400 under a load of 1 kg.

Cross-cut peeling test

Onto a hard coating layer formed on the molded article surface, were cut with a knife respectively 11 longitudinal and transversal lines with 1 mm intervals, to form 100 squares of 1 mm side. A cellophane adhesive type (mfd. by Sekisui Chemical Co., Ltd.) was sticked thereonto, and the adhesive type was peeled off towards the 90° direction. The results are expressed in terms of the number of squares in which the coating layer has not been peeled off.

Steel wool test

A hard-coated mold article was rubbed with #0000 steel wool and examined for the presence of scratches.

Steam treatment

The specimen was treated in an autoclave at 121° C. for 30 min.

Referential Example 1

Under nitrogen atmosphere, 200 parts by weight of cyclohexane, 2.0 parts by weight of 1-hexene, 15 parts by weight of a 15% by weight triethylaluminum solution in toluene and 5.0 parts by weight of triethylamine were added to 20 parts by weight of ethyltetracyclododecene and, while keeping the mixture at 20° C. and with stirring, 80 parts by weight of ethyltetracyclododecene and 9.0 parts by weight of a 20% by weight titanium tetrachloride solution in toluene were continuously added thereto over a period of 60 minutes. Thereafter, the mixture was allowed to react for 1 hour, and then the reaction was stopped by addition of 5.0 parts by weight of ethyl alcohol and 2.0 parts by weight of water. The reaction liquid was warmed to 40° C. to hydrolyze the catalyst, then 3 parts by weight of calcium sulfate and 60 parts by weight of cyclohexane were added, and the excess water was removed. The precipitate containing metals thus deposited was removed by filtration to obtain 371 parts by weight of a clear polymer solution containing ethyltetracyclododecene ring-opening polymer.

Reference Example 2

To 750 parts by weight of a polymer solution obtained by repeating Referential Example 1, was added 15 parts by weight of Ni-kieselguhr catalyst (N 113, mfd. by Nikki Chemical Co., Ltd.). The mixture was placed in an autoclave and, with introduction of hydrogen thereinto, subjected to hydrogenation at a pressure of 50 kg/cm$^2$ and a temperature of 200° C. for 3 hours. After completion of the reaction, the reaction mixture was diluted by addition of 700 parts by weight of cyclohexane and filtered to remove the catalyst, to obtain 1,350 parts by weight of an ethyltetracyclododecene ring-opening polymer hydrogenation product solution.

Then, 550 parts by weight of the solution was poured into 1,500 parts by weight of isopropyl alcohol with stirring to coagulate the ring-opening polymer hydrogenation product. The coagulated ring-opening polymer hydrogenation product was collected by filtration, washed twice with 300 parts by weight of isopropyl alcohol, and then dried in a rotary vacuum dryer at 5 torr and 120° C. for 48 hours to obtain 52 parts by weight of an ethyltetracyclododecene ring-opening polymer hydrogenation product.

The ring-opening polymer hydrogenation product had a number average molecular weight of 28,000 as determined by gel permeation chromatography and calculated as polystyrene, weight average molecular weight of 58,000, hydrogenation rate of 99.8% or more, glass transition temperature of 142° C. as determined by differential scanning colorimetry, and content of polymer component having a molecular weight of 2,000 or less of 0.1%.

Atomic adsorption analysis of a 10% by weight cyclohexane solution of the ring-opening polymer hydrogenation product showed that the contents of titanium atoms, nickel atoms and aluminum atoms in the hydrogenation products were, respectively, 4 ppm, 1.8 ppm and 2.21 ppm. Separately, 100 mg of the ring-opening polymer hydrogenation product was burned in a Dohrmann combustion apparatus (mfd. by Rosemount Analytical Division), then absorbed in 5 ml of pure water and analyzed by ion chromatography, to show a chlorine atom content of 2.7 ppm.

Referential Example 3

Nine hundred (900) parts by weight of a solution obtained by dissolving 100 parts by weight of the ring-opening polymer hydrogenation product obtained in Referential Example 2 in 800 parts by weight of 97% by weight cyclohexane was passed through a column 10 cm in internal diameter and 100 cm in length packed with 45 parts by weight of activated alumina (Neobead D, mfd. by Mizusawa Industrial Chemicals, Ltd.) such that the residence time may be 100 sec., and circulated for 24 hours. The solution was then poured into 2,500 parts by weight of isopropyl alcohol with stirring to coagulate the ring-opening polymer hydrogenation product. The coagulated ring-opening polymer hydrogenation product was collected by filtration, washed twice with 430 parts by weight of isopropyl alcohol, and then dried in a rotary vacuum drier at 5 torr and 120° C. for 48 hours, to obtain 78 parts by weight of an ethyltetracyclododecene ring-opening polymer hydrogenation product.

The ring-opening polymer hydrogenation product showed no difference in molecular weight and glass transition temperature from that of Referential Example 2, but showed contents of titanium atom, nickel atom, aluminum atom, and chlorine atom of 1 ppm (detection limit) or less, 0.1 ppm (detection limit) or less, 0.21 ppm, and 0.37 ppm, respectively.

Referential Example 4

To 99.8 parts by weight of the ethyltetracyclododecene ring-opening polymer hydrogenation product obtained in Referential Example 3 were added a rubber-like polymer (Tuftec H 1052 mfd. by Asahi Chemical Industry Co., Ltd., glass transition temperature: 0° C. or lower) and 0.05 parts by weight of an antioxidant (Irganox 1010, mfd. by Ciba-Geigy Limited), and the mixture was kneaded and extended through a twin-screw kneader (TEM-35B, mfd. by Toshiba Machine Co., Ltd., screw diameter 37 mm, L/D 32, number of revolution of screw 250 rpm, resin temperature 265° C., feed rate 10 kg/hour) to form pellet.

EXAMPLE 1

The pellet obtained in Referential Example 4 was injection-molded (clamping pressure 350 t, resin temperature 280° C., mold temperature 100° C.) to prepare a transparent, cylindrical container 200 mm in diameter, 130 mm in height and 3 mm in average thickness, and about 10 test pieces of 10 mm×50 mm×2.0 mm.

The test piece showed a total light transmittance of 90.2% on determination and thus a good transparency. It showed a turbidity of 0.1% on determination. In the molded container were placed 300 ml of an LB culture medium (aqueous solution containing 1% by weight of Bacto trypton, 0.5% by weight of yeast extract, 1% by weight of NaCl and 0.1 by weight of glucose, adjusted to pH 7.5), by of agar, and one of the test pieces, then capped with aluminum foil, and subjected to a steam sterilization treatment at 121° C. for 30 min.

After the treatment, the container was kept at 37° C. for 3 days. No growth of fungi was recognized.

The treatment container after the treatment has a good appearance and showed no cloudiness, crack, nor deformation due to heating in visual inspection. The test piece withdrawn from the container and cleared of the LB culture medium solidified with agar showed a turbidity of 0.27% and total light transmittance of 89.7% upon determination.

Separately, one of the test pieces was immersed in an aqueous sodium carbonate solution of pH 9, hydrochloric acid of pH 4, or ethanol for 48 hours. The test piece showed no change in appearance in visual observation, and also no change in turbidity and total light transmittance.

On the other hand, 200 g of distilled water was placed in a hard glass flask, then the flask was capped with a hard glass cap, steam-sterilized at 120° C. for 1 hour, cooled down to room temperature, allowed to stand for 24 hours, and the distilled water was recovered.

Further, one of the test pieces was subjected to ultrasonic washing in distilled water for 20 min. and then dried at 40° C. for 10 hours. The test piece was cut to a width of 10 mm, 20 g thereof was placed in a hard glass flask, and 200 g of distilled water was added. The flask was capped with a hard glass cap, steam-sterilized at 120° C. for 1 hour, cooled down to room temperature, then allowed to stand for 24 hours, and the distilled water was recovered.

The two kinds of distilled water thus obtained were analyzed by atomic absorption analysis, ion chromatography and combustion-nondispersive infrared gas analysis and, from the differences in the results of the analyses, the amounts of substances dissolved out from the test pieces were determined. The amounts were found to be as follows:

| | |
|---|---|
| titanium atom: | 0.1 ppm (detection limit) or less, |
| nickel atom: | 0.01 ppm (detection limit) or less, |
| aluminum atom: | 0.01 ppm (detection limit) or less, |
| chlorine atom: | 0.02 ppm (detection limit) or less, and |
| total organic carbon: | 2 ppm (detection limit) or less. |

The above-mentioned test piece was subjected to a dissolved-out substance test according to "the method of testing plastics for infusion" specified in Pharmacopoeia Japonica (12th revision). It was found that foaming disappeared in less than 3 min., difference in pH was −0.03, ultraviolet absorption was 0.007 and substances reducible by potassium permanganate was 0.15 ml and that the material had thus properties suitable for medical use.

Comparative Example 1

Polystyrene (Idemitsu Styrol HT53 mfd. by Idemitsu Petrochemical Co., Ltd., glass transition temperature 100° C.) was injection-molded in the same manner as in Example 1 at a resin temperature of 220° C. and mold temperature of 40° C.

The molded article was steam-sterilized in the same manner as in Example 1. The article deformed greatly and could not be used. The test piece after steam sterilization was cloudy, opaque, and no longer in the form of plate, so that the total light transmittance could not be determined.

EXAMPLE 2

The pellet obtained in Referential Example 4 was blow-molded at a mold temperature of 100° C., resin temperature of 290° C. and blow-in air pressure of 5 kg/cm$^2$ to obtain a container A having a cylindrical side face and one bottom face (20 mm in diameter, 40 mm in height and 2 mm in thickness) and a container B of a similar shape (200 mm in diameter, 130 mm in height and 3 mm in thickness).

A hard coating agent was prepared by dissolving 10 parts by weight of dispentaerythritol hexaacrylate, 10 parts by weight of 1,6-hexanediol diacrylate, 3 parts by weight of a photopolymerization initiator (Darocur 1173, mfd. by Merck Japan Limited), and 0.1 part by weight of a fluorine-containing surface active agent (FC-430, mfd. by Sumitomo 3M Limited) in 80 parts by weight of isopropyl alcohol.

The hard coating agent was coated on the container A obtained in Referential Example 1 by means of dipping while preventing the coating agent from contacting with the inside of the container. The film thickness was about 5 μm. After isopropyl alcohol was evaporated off by allowing the coating to stand at 50° C. for 1 min., the hard coating agent was cured by application of ultraviolet irradiation at 10,000 mJ/cm$^2$ using a high pressure mercury lamp for two min.

In the same manner as above, hard coating was applied onto the outside surface of the container B. The outside surface thus treated should no scratch in the steel wool test, no change in the oil resistance test, and a good adhesiveness of 100 squares/100 squares in the cross-cut peeling test. Further, it should no change in the steam treatment. It had a pencil hardness of 3H.

The coated container was immersed in methanol, acetone, toluene, and gasoline in such a way that there solvents might not enter the inside, and allowed to stand for 24 hours. No particular abnormality was recognized.

EXAMPLE 3

Hard coating treatment was conducted in the same manner as in Example 2 with the exception that the hard coating agent was changed to one obtained by dissolving 7 parts by weight of dipentaerythritol hexaacrylate, 3 parts by weight of 6-hexanediol diacrylate, 0.3 part by weight of a photopolymerization initiator (Darocur 1173, mfd. by Merck Japan Limited), and 0.1 part by weight of a fluorine-containing surface active agent (FC-430, mfd. by Sumitomo 3M Limited) in 90 parts by weight of isopropyl alcohol. The film thickness was 3 μm.

The hard-coated outside surface of the container B showed no scratch in the steel wool test, no change in the oil resistance test, and a good adhesiveness of 100 squares/100 squares in the cross-cut peeling test. Further, it showed no change in the steam treatment. The outside surface had a pencil hardness of 3H.

The coated container was immersed in methanol, acetone, toluene, or gasoline in such a way that these solvents might not enter the inside. No particular abnormality was recognized.

Comparative Example 2

The outside surface of the container B obtained in Example 2 was subjected to the steel wool test to find that scratches were formed severely. The surface developed cracks in the oil resistance test. It showed no change in the steam treatment. The outside surface had a pencil hardness of HB.

The container was immersed in methanol, acetone, toluene, or gasoline in such a way that these solvents might not enter the inside, and allowed to stand for 24 hours. No abnormality was recognized in the case of methanol or acetone, but the surface dissolved in the case of toluene or gasoline.

EXAMPLE 4

The ring-opening polymer hydrogenation product of Referential Example 3 was made into pellet and then molded in the same manner as in Example 1 except that neither rubber-like polymer nor antioxidant were added.

The test piece after molding showed a total light transmittance of 90.8% and thus had a good transparency. Its turbidity was found to be 0.06% upon determination.

An LB culture medium was supplemented with 2% by weight of agar, and steam-sterilized at 121° C. for 30 min. to form a gel. Before the gel solidified, 300 ml of the gel was placed in the container molded above, allowed to stand at room temperature for 6 hours, then capped with aluminum foil, and sterilized by irradiation of 25 kGy of γ ray.

After the above treatment, the container was kept at 37° C. for 3 days. No growth of fungi was recognized.

The transparent container after the treatment had a good appearance and showed no cloudiness, crack, nor deformation in visual observation. The test piece withdrawn from the container was cleared of the LB culture medium solidified with agar and then examined for turbidity and total light transmittance. The values thus determined showed no change as compared with those before the treatment.

Immersion in the respective solvents also showed no change like in Example 1. The amounts of dissolved-out substances determined in the same manner as in Example 1 were: titanium atom: 0.1 ppm (detection limit) or less, nickel atom: 0.01 ppm (detection limit) or less, aluminum atom: 0.01 ppm (detection limit) or less, chlorine atom: 0.02 ppm (detection limit) or less, and total organic carbon: 2 ppm (detection limit) or less.

The dissolved-out substance test showed that foaming disappeared in 3 min., difference in pH was −0.03, ultraviolet absorption was 0.06, and substances reducible by potassium permanganate was 0.13 ml and that the material had thus properties suitable for medical use.

EXAMPLE 5

To 100 parts by weight of the ring-opening polymer hydrogenation product obtained in Referential Example 3 was added 0.05 part by weight of pentaerythrityl-tetrakis[3-(3,5-di-t-butyl-4-hydroxyphenyl)propionate](Irganox 1010, an antioxidant, mfd. by Ciba-Geigy Limited, molecular weight 1177.7) and the mixture was kneaded in a twin-screw extruder to prepare pellet.

Molding was conducted in the same manner as in Example 1 except that the pellet obtained above was used in place of the pellet containing a rubber-like polymer kneaded therein.

The molded test piece showed a total light transmittance of 90.1% and thus had a good transparency. The turbidity was found to be 0.08% upon determination. In the same manner as in Example 4, an LB culture medium was placed in the molded container and sterilized. No growth of fungi was recognized. The transparent container after the treatment had a good appearance and showed no cloudiness, crack, nor deformation in visual inspection. The test piece showed no change in total light transmittance and turbidity.

The amounts of dissolved-out atoms were as follows: titanium atom: 0.1 ppm (detection limit) or less, nickel atom: 0.01 ppm (detection limit) or less, aluminum atom: 0.01 ppm (detection limit) or less, chlorine atom: 0.02 ppm (detection limit) or less, and total organic carbon: 2 ppm (detection limit) or less.

The above-mentioned kneaded pellet was subjected to a dissolved-out substance test according to "the method of testing plastics for infusion" specified in Pharmacopoeia Japonica (12th revision). It was found that foaming disappeared in less than 3 min., difference in pH was −0.05, ultraviolet absorption was 0.007, and substances reducible by potassium permanganate was 0.13 ml and that the material had thus properties suitable for medical use.

EXAMPLE 6

Pellet was obtained in the same manner as in Example 5 except that octadecyl-3-(3,5-di-t-butyl-4-hydroxyphenyl] propionate [Irganox 1070, an antioxidant mfd. by Ciba Geigy Limited, molecular weight 530.9) was used in place of pentaerythrityl-tetrakis[3-(3,5-di-t-butyl-4-hydroxyphenyl)propionate]. Then, molding was conducted in the same manner as in Example 1 except that the above-mentioned pellet was used in place of the pellet containing a rubber-like polymer kneaded therein.

The molded test piece showed a total light transmittance of 99.0% and thus had a good transparency. It showed a turbidity of 0.06% upon determination. In a sterilization treatment test conducted in the same manner as in Example 4, no growth of fungi was recognized. The transparent container after the treatment had a good transparency and showed no cloudiness, crack, nor deformation in visual inspection. The test showed also no change in total light transmittance and turbidity.

The amounts of dissolved-out atoms were found to be as follows: titanium atom: 0.1 ppm (detection limit) or less, nickel atom: 0.01 ppm (detection limit) or less, aluminum atom: 0.01 ppm (detection limit) or less, chlorine atom: 0.02 ppm (detection limit) or less, and total organic carbon: 2 ppm.

EXAMPLE 7

Pellet was prepared in the same manner as in Referential Example 4 except that 0.3 part by weight of a glycerol ether compound (wherein glycidol combines at a ratio of average 1.2 molecules per 1 repeating unit originating from nonylphenol, average molecular Weight 1,590) obtained by the reaction of a nonylphenol-formaldehyde condensation product (average number of condensation of nonylphenol component: 5.0) with glycidol was added in place of a rubber-like polymer, and injection molded in the same manner as in Example 1.

The molded test piece showed a total light transmittance of 88.0% and thus had a good transparency. It showed a turbidity of 0.90% upon determination. In a sterilization treatment test conducted in the same manner as in Example 1, no growth of fungi was observed, and the container after the treatment had a good appearance and showed no cloudiness, crack, nor deformation in visual inspection. The test piece showed a total light transmittance of 87.5% and turbidity of 1.1%.

The amounts of dissolved-out atoms were found to be as follows: titanium atom: 0.1 ppm (detection limit) or less, nickel atom; 0.01 ppm (detection limit) or less, aluminum atom: 0.01 ppm (detection limit) or less, chlorine atom: 0.02 ppm (detection limit) or less, and total organic carbon: 2 ppm (detection limit) or less.

EXAMPLE 8

The polymer obtained in Referential Example 3 was injection-molded (clamping pressure 350 t, resin temperature 280° C., mold temperature 100° C.) to form syringe cylinders of 18 mm outside diameter, 14 mm inside diameter, 110 mm length and 10 ml inner volume. The syringe cylinder was subjected to ultrasonic washing in distilled water for 20 min. and dried at 40° C. for 10 hours. Then the cylinder was steam-sterilized in a high pressure steam sterilizer at 120° C. for 20 min. No change was recognized in the shape of the syringe cylinder.

With three of the syringe cylinders, the respective front ends were closed with Teflon plugs. The cylinders were held in a holder with their front ends pointing downward, then respectively filled with 10 ml each of an aqueous vitamin $B_2$ solution having a concentration of 80 ppm, aqueous methamphetamine hydrochloride solution having a concentration of 300 ppm and aqueous tranexamic acid solution having a concentration of 1,000 ppm, and the rear ends were hermetically closed with Teflon plugs. The filled cylinders were allowed to stand still in the dark at room temperature for 30 days. Thereafter the solutions were analyzed by high performance liquid chromatography to show that the vitamin $B_2$ concentration was about 790 ppm, the methamphetamine hydrochloride concentration about 300 ppm, and the tranexamic acid concentration about 990 ppm.

EXAMPLE 9

In the same manner as in Example 8 except that the pellet obtained in Referential Example 4 was used in place of the polymer obtained in Referential Example 3, syringe, cylinders were molded and sterilized. No change in shape was recognized. Further, in the same manner as in Example 8, the respective aqueous solutions were filled in the cylinders, allowed to stand still for 30 days, and analyzed to show that the vitamin $B_2$ concentration was about 80 ppm, the methamphetamine hydrochloride concentration about 300 ppm, and the tranexamic acid concentration about 990 ppm.

EXAMPLE 10

The pellet obtained in Referential Example 4 was injection-blow-molded at a resin temperature of 280° C. and a mold temperature of 120° C. to form a bottle of 25 mm outside diameter, 60 mm height and 20 ml inner volume.

The bottle was subjected to ultrasonic washing in distilled water for 20 min., then dried thoroughly, and steam-sterilized at 120° C. for 30 min. Thereafter it was filled with 20 ml of an aqueous vitamin $B_2$ solution having a concentration of 800 ppm, and hermetically closed with a Teflon plug. The bottle was allowed to stand still in the dark at room temperature for 30 days, and then the aqueous solution was analyzed by high performance liquid chromatography. Resultantly, vitamin $B_2$ concentration was 800 ppm, thus showing virtually no change.

EXAMPLE 11

With 100 parts by weight of the pellet of ZEONEX 80 (a thermoplastic saturated norbornene polymer mfd. by Nippon Zeon Co., Ltd., glass transition temperature 140° C., refractive index at 30° C. 1.5241) were mixed 0.2 part by weight of a phenol-type antioxidant (pentaerythrityltetrakis(3-(3,5-di-tert-butyl-4-hydroxyphenyl)propionate) and 0.2 part by weight of an styrene-ethylene-butadienestyrene block copolymer (Tuftec H1051, mfd. by Asahi Chemical Industry Co., Ltd., crumb-like, refractive index at 30° C. 1.5173), and the mixture was kneaded in a twin-screw kneader (Laboplastomill, mfd. by Toyo Seiki K.K., different direction, resin temperature 180° C., number of rotation of screw 50 rpm). The torque decreased gradually to become approximately constant 4 minutes after the initiation of kneading. Then, kneading was continued for further 10 min.

The mass of the resulting composition was taken out, and formed into a plate of 20 mm×15 mm×3 mm thickness with a hot press (resin temperature 200° C., 300 kgf/cm², 3 min.). The plate was transparent and showed a light transmittance in the range of 400–700 nm of 90.1% at the minimum. Aluminum film of 100 nm thickness was formed on the plate by vacuum vapor deposition and subjected to the cross-cut peeling test. The test gave a value of 100%, showing a good adhesiveness.

The plate was sliced to a thickness of about 0.05 μm, the polystyrene part was stained with ruthenium and examined with a transmission electron microscope. It was observed that the rubber-like polymer assumed a structure of approximately spherical microdomains of about 0.02 μm diameter, in the matrix of norbornene polymer. The pellet had a glass transition temperature of 140° C.

The same kneaded mass of the polymer composition was injection-blow-molded at a resin temperature of 260° C. to form cylindrical, narrow-mouthed bottles with an average thickness of the cylindrical part of 3 mm and inner volume of 100 ml. The container was transparent. A part of the container was cut out and examined for haze with haze meter to obtain a value of 0.5%.

The container was heated in boiling water at 100° C. for 30 min., in a steam at 121° C. for 30 min., or allowed to stand at 85° C. and 90% R.H. for 48 hours. In all cases, no change in appearance was recognized by observation with naked eye and with a microscope at a magnification of 50.

EXAMPLE 12

With 100 parts by weight of ZEONEX 280 were mixed 0.2 part by weight of a phenol-type antioxidant (pentaerythrityl-tetrakis( 3-(3,5-di-t-butyl-4-hydroxyphenyl)propionate)) and 0.3 part by weight of a styrene-ethylene-butadiene-styrene block copolymer (Tuftec 1051, mfd. by Asahi Chemical Industry Co., Ltd.), and the mixture was kneaded and extruded into the form of strand with a twin-screw kneader (TEM-35B, mfd. by Toshiba Machine Co., Ltd., same direction, screw diameter 37 mm, L/D 31.1, resin temperature 235° C., number of screw rotation 150 rpm, residence time about 2 min., processing rate 10 kg/hr.) and cut with a strand cutter to obtain pellet.

The pellet was sliced to a thickness of about 0.05 μm, the polystyrene part was stained with ruthenium tetraoxide, and examined with a transmission electron microscope. It was observed that the rubber-like polymer assumed a structure of approximately spherical microdomains of about 0.01 μm diameter, in the matrix of the norbornene polymer. The pellet had a glass transition temperature of 139° C.

The pellet was injection-molded at a resin temperature of 270° C. to form a plate of 50 mm×50mm×3.0 mm thickness. The plate showed a light transmittance in the range of 400–700 nm of 90.5% at the minimum. An acrylic lacquer-type, black, light-shielding coating material (Acrylic #1000(A), mfd. by Kansai Paint Co., Ltd.) was spray-coated on the plate and dried in an air over at 50° C. for 30 min. to form a coating of about 0.15 mm thickness. The coated film was subjected to the cross-cut peeling test. The test gave a value of 100%, showing a good adhesiveness.

EXAMPLE 13

Pellet was prepared in the same manner as in Example 12 except that 0.7 part by weight of a styrene-isoprene-styrene block copolymer (Quintac 3421, mfd. by Nippon Zeon Co., Ltd., refractive index at 30° C. 1.5276) was used in place of 0.3 part by weight of styrene-ethylene-butadiene-styrene block copolymer.

The pellet was stained and observed in the same manner as in Example 11. It was revealed that the copolymer assumed a structure of approximately spherical microdomains about 0.19 μm in diameter. The pellet had a glass transition temperature of 130° C.

A plate 3.0 mm in thickness was prepared in the same manner as in Example 11. The plate showed a light transmittance in the range of 400–700 nm of 90.2% at the minimum. An aluminum film 100 nm in thickness was formed on the plate by vacuum vapor deposition and subjected to the cross-cut peeling test. The test showed a value of 100%, thus showing a good adhesiveness.

Comparative Example 3

Pellet was prepared in the same manner as in Example 11 except that no rubber-like polymer was mixed, and injection-molded to form a plate 3.0 mm in thickness. The plate showed a light transmittance in the range of 400–700 mm of 90.8% at the minimum. An aluminum film was formed in the same manner as in Example 11 and subjected to the crosscut peeling test. The test showed an adhesiveness of 86%.

Comparative Example 4

Kneading was conducted in the same manner as in Example 11 except that 8 parts by weight of styrene-isoprene-styrene block copolymer was mixed instead of 0.5 part by weight. The torque of the kneader decreased gradually and reached a constant value. Ten minutes thereafter the kneading was finished.

The resulting composition was stained and observed in the same manner as in Example 11. It was recognized that the rubber-like polymer formed, though partly, spherical microdomains about 0.25 μm in diameter and spherical particles about 2–5 μm in diameter formed by coagulation of the microdomains.

The composition was molded into a plate of 20 mm×15 mm×15 mm×3.0 mm thickness under the same conditions as in Example 11. An aluminum film was formed thereon in the same manner as in Example 11 and subjected to the cross-cut peeling test, to show a good adhesiveness of 100%. However, the plate was turbid even in visual inspection, and showed a light transmittance of only 30–42% in the range of 400–700 nm.

Comparative Example 5

With 100 parts by weight of the pellet of ZEONEX 280 was mixed 0.2 part by weight of a phenol-type antioxidant (pentaerythrityl-tetrakis(3-(3,5-di-t-butyl-4-hydroxyphenyl-)propionate)) and the mixture was kneaded in a twin-screw kneader (Laboplastomill, mfd. by Toyo Seiki K.K., different direction, resin temperature 180° C., number of screw rotation 50 rpm). At the time when the mixture had been kneaded for 3 min., 3.0 parts by weight of a styrene-ethylene-butadiene-styrene block copolymer (Tuftec H1051, mfd. by Asahi Chemical Industry Co., Ltd., the same as that used in Example 12) was added, and the mixture was kneaded for further 1 min.

The kneaded mixture was formed into a plate, stained and observed in the same manner as in Example 12. The rubber-like polymer was in the form of layers each about 1 μm thickness and was not dispersed uniformly.

The kneaded mixture was injection-molded in the same manner as in Example 12 to form a plate 3.0 mm in thickness. The plate showed a light transmittance in the same of 400–700 nm of 72% at the minimum. When an aluminum film was formed thereon in the same manner as in Example 12, a pattern in the form of Spots developed on the surface. When subjected to the cross-cut peeling test, the film showed an adhesiveness of 54%.

As set forth above, the medical implements of the present invention are excellent in heat resistance, moisture resistance and transparency. Medicines are scarcely adsorbed thereto, and little of organic substances are dissolved out therefrom. Hence, they do not cause the deterioration of medicines and other agents that are in contact therewith. Further, by applying hard coating on the parts which do not come in contact with medicines or such, the hardness and chemical resistance of the hard-coated parts can be improved. Furthermore, among the polymer compositions used for these medical implements, those wherein the compounding ingredient has been made to assume the form of microdomains are particularly excellent in transparency and can be used as also optical materials excellent in adhesiveness to various coating materials and films.

What is claimed is:

1. A medical implement consisting essentially of a thermoplastic norbornene polymer wherein the thermoplastic norbornene polymer has a number average molecular weight of 10,000–200,000 as determined by gel permeation chromatographic analysis in toluene and calculated as polystyrene, wherein the thermoplastic norbornene polymer contains 0.01 to 10% by weight of a compounding ingredient incompatible therewith, and wherein the difference in refractive index between the compounding ingredient and the thermoplastic norbornene polymer is 0.3 or less.

2. A medical implement according to claim 1, wherein the thermoplastic norbornene polymer has a glass transition temperature of 105° C. or more.

3. A medical implement according to claim 1, wherein the thermoplastic norbornene polymer has 1% by weight or less of polymer components having a number average molecular weight of 2,000 or less.

4. A medical implement according to claim 1, wherein the thermoplastic norbornene polymer contains 1 ppm or less of a transition metal.

5. A medical implement according to claim 1, wherein the thermoplastic norbornene polymer contains 1 ppm or less of chlorine.

6. A medical implement according to claim 1, wherein the thermoplastic norbornene polymer contains 3,000 ppm or less of an antioxidant having a molecular weight of 600 or higher.

7. A medical implement according to claim 1, wherein the thermoplastic norbornene polymer contains 0.01–5% by weight of at least one partial etherification product and one partial esterification product of a polyhydric alcohol.

8. A medical implement according to claim 1, wherein the medical implement is a container for a medicine.

9. A medical implement according to claim 8, wherein the container is sterilized after being filled with the medicine.

10. A medical implement according to claim 1, wherein the implement is an optical implement.

11. A medical implement according to claim 1, wherein a hard coating layer is formed on the outside of at least a part thereof.

12. A medical implement according to claim 11, wherein the hard coating layer is formed by curing an ultraviolet curable hard coating agent.

13. A medical implement according to claim 1, wherein the difference in refractive index between the compounding ingredient and the thermoplastic norbornene polymer is 0.02 or less.

14. A medical implement according to claim 13, wherein the compounding ingredient is an elastomeric polymer dispersed as microdomains in the thermoplastic norbornene polymer.

15. A medical implement according to claim 14, wherein the diameter of the microdomains is 0.3 μm or less.

16. A medical implement according to claim 14, wherein the elastomeric polymer has a glass transition temperature of 40° C. or lower.

17. A medical implement according to claim 14, wherein the elastomeric polymer is selected from the group consisting of block copolymers of an aromatic vinyl monomer with a conjugated diene monomer, random copolymers of an aromatic vinyl monomer with a conjugated diene monomer and hydrogenation products thereof, and norbornene-based elastomeric polymers.

18. A medical implement according to claim 14, wherein the elastomeric polymer is selected from the group consisting of styrene-butadiene block copolymers, styrene-butadiene-styrene block copolymers, styrene-isoprene block copolymers, styrene-isoprene-styrene block copolymers, and hydrogenated products thereof, and styrene-butadiene random copolymers.

19. A medical implement according to claim 14, wherein the thermoplastic norbornene polymer is an ethyltetracyclododecene ring-opened hydrogenation polymer and the elastomeric polymer is a styrene-ethylene-butadiene-styrene block copolymer.

20. A medical implement according to claim 1, wherein the thermoplastic norbornene polymer contains 5 to 0.5% by weight of the compounding ingredient, and the difference in refractive index between the compounding ingredient and the thermoplastic norbornene polymer is 0.2 or less.

21. A medical implement according to claim 1, wherein the thermoplastic norbornene polymer contains less than 0.5% by weight of the compounding ingredient.

* * * * *